United States Patent [19]

Futami et al.

[11] Patent Number: 4,778,832
[45] Date of Patent: Oct. 18, 1988

[54] DENTAL PRECISE IMPRESSION MATERIALS COMPRISING SILICONE

[75] Inventors: Shunichi Futami, Nagareyama; Satoshi Terauchi, Gotenba, both of Japan

[73] Assignee: G-C Dental Industrial Corp., Tokyo, Japan

[21] Appl. No.: 60,523

[22] Filed: Jun. 11, 1987

[30] Foreign Application Priority Data

Jul. 7, 1986 [JP] Japan ................ 61-157851

[51] Int. Cl.$^4$ .................................. A61K 6/10
[52] U.S. Cl. ...................... 523/109; 524/17; 106/35
[58] Field of Search .............. 106/35; 523/109; 524/17

[56] References Cited

U.S. PATENT DOCUMENTS

| 4,007,153 | 2/1977 | Smith | 523/109 |
| 4,449,938 | 5/1984 | Pollak | 106/35 |
| 4,657,959 | 4/1987 | Bryan | 524/266 |
| 4,704,416 | 11/1987 | Eck et al. | 524/17 |

Primary Examiner—Theodore Morris
Attorney, Agent, or Firm—Oblon, Fisher, Spivak, McClelland & Maier

[57] ABSTRACT

A dental precise impression material comprises condensation or addition type room temperature-vulcanizing silicone, and further contains 0.1 to 10.0 weight % of at least one protein soluble or slightly soluble in water optionally with 0.05 to 5.0 weight % of at least one hydrophilic nature-affording agent selected from hydrophilic silicone oils and nonionic surface active agents.

14 Claims, No Drawings

DENTAL PRECISE IMPRESSION MATERIALS COMPRISING SILICONE

BACKGROUND OF THE INVENTION

1. Field of the Invention

The present invention relates to a moulding material (hereinafter referred to as the impression material) used for the preparation of the oral tissue models required for the preparation of dental prostheses such as crowns, inlays or dentures and, more especially, to a dental precise impression material comprising silicone, which is designed to be used for precise impression material.

2. Statement of the Prior Art

Dental impression materials are generally broken down into non-elastic and elastic types.

The non-elastic impression materials may include those formed of wax, gypsum, modelling compounds and the like. With the non-elastic impression materials, however, it is hardly possible to achieve any precise moulding (impression) of the teeth, arrangement of the teeth, jaw and mucosa, each having a complicated shape and form and including undercuts, of the oral cavity, since they undergo no elastic deformation. Because of this, general moulding (impression) of the oral cavity is presently carried out with modelling compounds to form an individual tray, which is merely used in combined impression with other precise impression materials.

The elastic impresstion materials may include those formed of agar, alginates, polysulfide rubber, polyether rubber, silicone rubber and the like. The elastic impression materials make it possible to take the impressions of the teeth, arrangement of the teeth, jaw and mucosa, each having a complicated shape and form and including undercuts, of the oral cavity, since they are elastically deformable so that, when removing the impression from within the oral cavity, their deformation, if any, is restorable to the original form.

While the agar or alginate impression materials are advantageous in that they show a suitable degree of elasticity from the clinical point-of-view, and are easy to handle and relatively inexpensive, they are disadvantageous in that they undergo a considerable extent of permanent deformation, and that the impression obtained therefrom and taken out of the oral cavity changes largely in dimensions with the lapse of time due to their large amount of moisture content and tends to be readily torn due to their low tear strength. For those reasons, they are mainly used for snap impression.

The synthetic rubber-based impression materials obtained by using a raw material e.g., polysulfide rubber, polyether rubber and silicone rubber are used for precise impression, since they show a suitable degree of elasticity from the clinical point-of-view, are easy to handle and give rise to fairly small permanent deformation, and provide cured products which show only limited dimensional changes with the lapse of time and high tear strength.

Of the types of synthetic rubber forming the impression materials, the polysulfide rubber is disdvantageous in that it gives out strong offensive odor, and is cured too slowly; and the polyether rubber is of reduced elasticity and hard, and is largely affected by moisture. However, the silicone rubber is most frequency used as the impression material, because it provides a material which is tasteless and odorless, is sharply cured, excels in elasticity and exhibits excellent dimensional stability owing to its extremely limited dimensional change.

Depending upon the curing manner involved, the silicone rubber is classified into the condensation type and the addition type. Such room temperature-vulcanization silicone rubber is utilized as the dental silicone impression material. In general, one of the condensation type silicone impression material is available on one hand in the form comprising a base component consisting of a hydroxydimethyl polysiloxane having hydroxide groups at its both terminals and a catalyst component consisting of an alkyl orthosilicate and an organic tin compound which, in use, are mixed and kneaded together by an operator (typically a dentist) to prepare a mixture, which is then subjected to condensation vulcanization and setting at normal temperature to provide elastic silicone rubber, whereas the other is available in the form comprising a base component consisting of a hydroxydimethyl polysiloxane having hydroxide groups at its both terminals, a crosslinker (reactor) component consisting of alkyl orthosilicate and a catalyst component consisting of an organic tin compoubnd which, in use, are mixed and kneaded together by an operator to obtain a mixture, which is then subjected to condensation vulcanization and setting at normal temperature to provide elastic silicone rubber.

On the other hand, the addition type impression materials are generally available in the form comprising a base component consisting of a hydrogen polymethylsiloxane and a catalyst component consisting of a vinyl polymethylsiloxane having a vinyl group and a platinum catalyst added thereto, which, in use, are mixed and kneaded together by an operator to obtain a mixture, which is then subjected to addition vulcanization and setting at normal temperature to provide elastic silicone rubber.

The silicone impression materials based on such silicone rubber have the following excellent features:

1. They are readily mixable and kneadable.
2. They are sharply set in the oral cavity.
3. They excel in elastic recovery.
4. The surface of a gypsum model is smooth.
5. They provide a set body which undergoes only limited dimensional changes and, hence, excels in dimensional stability.
6. They are tasteless and odorless.

Thus, the best use is now made of the silicone impression materials.

With the silicone impression materials, however, it is difficult to take the precise impressions of the details of the oral cavity and, hence, reproduce precisely the details of the oral cavity on a gypsum model, when the oral cavity is wetted with blood, saliva or other fluids. This is because the silicone rubber possesses water repellency as one of its properties.

More specifically, when the oral cavity is wetted with saliva blood, or other fluids at the time of taking the impression of the oral cavity, the blood, saliva or other fluids are forced into the details such as interdentiums, margins of the teeth or pits and fissures in the teeth by the silicone impression material, and are allowed to remain there, since the silicone impression material shows unsatisfactory compatibility with respect to blood, saliva or other fluids. There is now a tendency that impression is carried out in that state, which renders it difficult to take detailed and precise impressions. At the time of impression, it is thus required for an operator to blow air to the regions of the oral cavity, the impressions of which are to be taken, followed by sufficient drying. This operation is troublesome for not only an operator but also a patient, and is especially difficult to apply to an infant or bleeding regions. At the time of the preparation of a gypsum model, there is a tendency that gypsum slurry is repelled on the registered surface of the impression taken, thus rendering it hard to cast it into the details of the registered surface and bringing about easy entrainment of air bubbles therein, since that surface shows unsatisfactory compatibility with respect to the gypsum slurry. It is thus difficult to precisely transfer the details of the registered surface onto the gypsum model. For that reason, it is required for an operator to cast the gypsum slurry into the details of the registered surface, while applying it thereonto in small portions by means of a brush. This operation needs careful attention, and is very troublesome for an operator. In order to solve the above-mentioned problems arising from the unsatisfactory wettability and compatibility which the silicone impression material show with respect to saliva, blood or other fluids or gypsum slurry, the addition of nonionic surface active agents to the silicone impression materials has hitherto been considered.

However, large amounts of such nonionic surfactants have had to be added to the silicone impression materials for the purpose of eliminating the wettability and compatibility problems. As a result, other problems arise, such as deteriorations of the physical properties due to inhibited setting reaction of silicone rubber and surface roughening of the gypsum model.

SUMMARY OF THE INVENTION

The present inventors have made intensive and extensive studies with a view to providing a solution to the problems without interferring with the setting reaction of silicone rubber, said problems arising from the unsatisfactory compatibility the silicone impression materials show with respect to blood, saliva or other fluids present in the oral cavity because of the water repellency of silicone rubber and the unsatisfactory compatibility the registered surface of the impression taken exhibits with respect to gypsum slurry. In consequence, it has unexpectedly been found that such compatibility problems can effectively be solved by adding to the silicone impression materials at least one protein soluble or slightly soluble in water or a combination of said protein with at least one hydrophilic nature-affording agent selected from hydrophilic silicone oils and nonionic surface active agents.

According to one aspect of the present invention, there is provided a dental precise impression material formed of condensation or addition type room temperature-vulcanizing silicone, which is characterized in that it further contains 0.1 to 10.0 weight % of at least one protein soluble or slightly soluble in water.

According to another aspect of the present invention, there is provided a dental precise impression material formed of condensation or addition type room temperature-vulcanizing silicone, which is characterized in that it further contains 0.1 to 10.0 weight % of at least one protein soluble or slightly soluble in water, and 0.05 to 5.0 weight % of at least one hydrophilic nature-affording agent selected from hydrophilic silicone oils and nonionic surface active agents.

DETAILED DESCRIPTION OF THE PREFERRED EMBODIMENTS

The protein soluble or slightly soluble in water shows satisfactory affinity with respect to saliva, blood or other fluids. Accordingly, if that protein is previously contained in the silicone impression materials, then the property of silicone rubber that repels blood, saliva or other fluids is reduced or limited so that the unsatisfactory compatibility of the silicone impression materials with respect thereto is improved. The protein soluble or slightly soluble in water does not interfere with the addition or condensation vulcanization of silicone rubber whatsoever and, hence, may not possibly give rise to a lowering of the physical properties of the silicone impression materials.

Therefore, the silicone impression materials containing the protein soluble or slightly soluble in water still have the same satisfactory features as those of the conventional silicone impression materials. Since the impression materials according to the present invention completely force the blood, saliva and other fluids out of the details such as interdentiums, margins of the teeth and pits and fissures in the teeth, they can be cast into such details to achieve precise impression, even when the oral cavity is wetted with blood, saliva and other fluids at the time of impression. At the time of preparing a gypsum model, the materials according to the present invention reduce or limit the repelling action of silicone rubber upon gypsum slurry, so that the wettability of the gypsum slurry with respect to the registered surface of the impression is improved, and, in particular, the gypsum slurry is cast into the details of the registered surface of the impression without recourse to any operation for applying it on that surface in small portions by means of a brush and with no substantial fear of air bubble entrainment, whereby the details of the registered surface of the impression can precisely be transferred onto the gypsum model. When used in combination with the protein soluble or slightly soluble in water, the hydrophilic nature-affording agents, such as hydrophilic silicone oils and nonionic surface active agents are effective, even in a small amount, for complete elimination of the water repellancy of silicone rubber. Especially where impression is carried out while the oral cavity is wetted with water just after washing with water, or the impression of a gypsum model wetted with water is taken to obtain a duplicate impression on the basis of that gypsum model, the wettability of silicone rubber with respect to the surface of the oral cavity, the impression of which is to be taken, and the surface of the gypsum model is much more improved, as compared with sole addition of the protein soluble or slightly soluble in water to the silicone impression materials.

The proteins usable for the present invention include simple, conjugated and derived proteins soluble or slightly soluble in water. Albumin, globulin, gluten, histone, protamine, etc. may be mentioned for the simple proteins; casein, vitellin, keratin, phosvitin, albumin tannate, gelatin tannate, etc. for the conjugated proteins; and gelatin, proteose, peptone, etc. for the derived proteins. Among them, preference is given to albumin, protamine, gelatin, peptone, casein, albumin tannate and gelatin tannate. These proteins soluble or slightly soluble in water may be added alone or in combination to the silicone impression materials.

Water-insoluble proteins do not lend themselves to the present invention, since they have no affinity effect upon saliva and blood. The amount of the proteins, soluble or slightly soluble in water, added to the silicone impression materials should inevitably be determined, taking into consideration their affinity effect upon saliva and blood, their workability and elasticity and their compatibility with respect to gypsum.

That is to say, when used in an amount of below 0.1 weight % with the silicone impression materials, the protein soluble or slightly soluble in water shows on the one hand no affinity effect upon saliva and blood. On the other hand, the use of that protein in an amount exceeding 10.0 weight % is unsuitable, because the elastic properties, especially permanent deformation, of the silicone impression materials deteriorate too largely to take precise impressions, and the solidification reaction of gypsum is inhibited, resulting in surface roughening of a gypsum model. Therefore, it is preferred that the amount of the protein soluble or slightly soluble in water to be contained in the silicone impression materials is in the range of 0.1 to 10.0 weight %.

Mentioned below are the hydrophilic nature-affording agents, such as hydrophilic silicone oils and non-ionic surfactants, to be added to the silicone impression materials in combination with the protein soluble or slightly soluble in water. Suitable hydrophilic silicone oils may include polyether-modified silicone oil and alcohol-modified silicone oil. Suitable nonionic surface active agents may include those having either an alkyl group, viz., a lipophilic group, combined with a hydrophilic group, or a hydrophilic group combined with a fluorocarbon group wherein the hydrogen atoms in an alkyl group, viz., a lipophilic group are substituted with fluorine. Ionic surface active agents are unsuitable, since they inhibit the setting reaction of silicone rubber, and roughen the surface of gypsum models. The non-ionic surface active agents usable in the present invention and having an alkyl group, that is a lipophilic group, combined with a hydrophilic group include:

(A) ether types wherein the number of addition moles of ethylene oxide or propylene oxide is 1 to 30, and an alkyl group has 12 to 22 carbon atoms, such as polyoxyethylene alkyl ether, polyoxyethylene polyoxypropylene alkyl ether and polyoxyethylene alkyl phenyl ether, (B) partial ester types of polyhydric alcohols and fatty acids having 12 to 22 carbon atoms, such as sorbitan.fatty acid esters, glycerin.fatty acids esters, polyglycerin.fatty acid esters, ethylene glycol.fatty acid esters, polyethylene glycol.fatty acid esters, propylene glycol.fatty acid esters and pentaerythritol.fatty acid esters, (C) ether ester types wherein the number of addition moles of ethylene oxide is 1 to 30, and a fatty acid has 12 to 22 carbon atoms, such as polyoxyethylene sorbitan.fatty acid esters, polyoxyethylene sorbitol.fatty acid esters, polyoxyethylene mannitan.-fatty acid esters, polyoxyethylene glyceryl fatty acid esters, and polyoxyethylene propylene glycol.mono-fatty acid esters, and (D) ester types of ethylene oxide obtained by addition polymerization, wherein the number of addition moles of ethylene oxide is 1 to 30, such as polyoxyethylene castor oil.hardened castor oil, polyoxyethylene lanolin derivatives, polyoxyethylene phitosterol and polyolxyethylene beeswax derivatives.

The nonionic surface active agents having a hydrophilic group combined with a fluorocarbon group wherein the hydrogen atoms in the alkyl group, viz., a lipophilic group are substituted with fluorine are represented by the following general formulae.

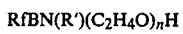

wherein
Rf is a fluorinated aliphatic or aromatic group having 1 to 20 carbon atoms provided that the aliphatic group may be straight, branched or cyclic,
B is a divalent connecting group (e.g., $-SO_2-$ and $-CO$),
R' is a hydrogen atom or an alkyl group having 1 to 20 carbon atoms, and
l, m and n each are an integer of 1 to 50.

The more the amount of the hydrophilic nature-affording agent used with the silicone component in the present invention, such as hydrophilic silicone oils and nonionic surfactants, the more remarkable the hydrophilic effect. However, that agent used in an amount exceeding 5.0 weight %, on the one hand, retards the setting reaction of the silicone impression materials, and inhibits the solidification reaction of gypsum and thereby roughens the surface of gypsum models. When that agent is used in an amount of below 0.05 weight %, on the other hand, no sufficient hydrophilic nature-affording effect is obtained. Thus, the amount of the hydrophilic nature-affording agent is suitably in the range of 0.05 to 5.0 weight %. It is understood that these hydrophilic nature-affording agents may be used alone or in combination with respect to the silicone impression materials.

In most cases, the silicone impression materials generally comprise either two-component systems consisting of base and catalyst components or three-component systems consisting of base, catalyst and reactor components. The present invention is applicable to any one of the combinations of the proteins soluble or slightly soluble in water with the hydrophilic nature-affording agents, as long as the silicone impression materials contain the required amounts of at least one of said proteins and at least one of said agents selected from hydrophilic silicone oils and nonionic surface active agents.

The silicone impression material used in the present invention may be any one of the room temperature vulcanizing silicone materials of the condensation or addition type, and may typically comprise the following components:

A. Condensation Type Silicone Impression Materials
(a) Hydroxydimethyl polysiloxanes having hydroxide groups at its both terminals.
(b) Crosslinkers, typically, ortho- or poly-ethyl silicates having an ethoxy group
(c) Condensation vulcanization catalysts, typically, organometallic compounds such as dibutyltin acetate, dibutyltin laurate and lead octenoic acid.
(d) Fillers, typically, diatomaceous earth, calcium carbonate, silicic acid, calcium sulfate, zirconium silicate, zirconium oxide, titanium oxide and zinc oxide. Alternatively, fillers surface-treated with resins, silane or the like.

(e) If necessary, coloring matters, perfumes, fluidity regulators, plasticizers and the like.

B. Addition Type Silicone Impression Materials (1) Vinylpolymethyl siloxanes having a vinyl-terminated group.
(2) Hydrogen polymethyl siloxanes having an active hydrogen-terminated group.
(3) Addition vulcanization catalysts, typically, platinum base catalysts.
(4) Fillers, typically, diatomaceous earth, calcium carbonate silicic acid, calcium sulfate, zirconium silicate, zirconium oxide, titanium oxide and zinc oxide. Alternatively, fillers surface-treated with resins, silane or the like.
(5) If necessary, coloring matters, perfumes, fluidity regulators, plasticizers and the like.

EXAMPLES

The present invention will now be explained with reference to the following non-restrictive examples.

EXAMPLE 1

Condensation Type Silicone Impression Material

| (i) | | |
|---|---|---|
| | Hydroxydimethyl polysiloxane | 70 weight % |
| | Silicic anhydride | 25 weight % |
| | Titanium oxide | 5 weight % |
| | | 100 weight % |

The ingredients (i) were charged with 6.5 weight % of albumin in a kneader, where they were sufficiently mixed and kneaded together for 1 hour into a base component.

| (ii) | | |
|---|---|---|
| | Dibutyltin laurate | 4 weight % |
| | Vaseline | 70 weight % |
| | Polyethyl silicate | 25 weight % |
| | Red oxide | 1 weight % |
| | | 100 weight % |

The ingredients (ii) were charged in a kneader, where they were sufficiently mixed and kneaded together for 1 hour into a catalyst component.

Equal amounts of the base component and the catalyst component were mixed and kneaded together for 30 seconds on a mixing pad with the use of a spatula.

EXAMPLE 2

Condensation Type Silicone Impression Material

The ingredients (i) of Example 1 were charged with 3.0 weight % of protamine and 3.5 weight % of polyether-modified silicone oil (manufactured by Shinetsu Kagaku K.K., and available under the trade name of KF 352) in a kneader, where they were sufficiently mixed and kneaded together for 1 hour into a base component.

Equal amounts of the base component and the catalyst component prepared in Example 1 were kneaded and mixed together on a mixing pad for 30 seconds with the use of a spatula.

EXAMPLE 3

Condensation Type Silicone Impression Material

The ingredients (i) of Example 1 were charged with 4.2 weight % of albumin tannate, 3.0 weight % of sorbitan.caprilic acid ester and 1.5 weight % of alcohol-modified silicone oil (manufactured by Shinetsu Kagaku K.K., and available under the trade name of KF 851) in a kneader, where they were sufficiently mixed and kneaded together for 1 hour into a base component.

Equal amounts of the base component and the catalyst component prepared in Example 1 were kneaded and mixed together on a mixing pad for 30 seconds with the use of a spatula.

EXAMPLE 4

Condensation Type Silicone Impression Material

The ingredients (i) of Example 1 were charged with 0.5 weight % of albumin and 4.8 weight % of ethylene glycol.caprilic acid ester in a kneader, where they were sufficiently mixed and kneaded together for 1 hour into a base component.

Equal amounts of the base component and the catalyst component prepared in Example 1 were kneaded and mixed together on a mixing pad for 30 seconds and with the use of a spatula.

EXAMPLE 5

Condensation Type Silicone Impression Material

| (i) | | |
|---|---|---|
| | Hydroxydimethyl polysiloxane | 75 weight % |
| | Diatomaceous earth | 25 weight % |
| | | 100 weight % |

The ingredients (i) were charged with 4.4 weight % of gelatin tannate in a kneader, where they were sufficiently mixed and kneaded together for 1 hour into a base component.

| (ii) | | |
|---|---|---|
| | Dibutyltin laurate | 30 weight % |
| | Vaseline | 45 weight % |
| | Paraffin wax | 25 weight % |
| | | 100 weight % |

The ingredients (ii) were charged in a kneader, and were mixed and kneaded together for 30 minutes, while heated to 70° C., thereby preparing a catalyst component.

| (iii) | | |
|---|---|---|
| | Silicone oil | 70 weight % |
| | Ethyl silicate | 30 weight % |
| | | 100 weight % |

The ingredients (iii) were charged with 1.5 weight % of sorbitan.monocaprilic acid ester in a mixer, where they were sufficiently mixed together for 20 minutes into a reactor component.

Ten (10) parts by weight of the base component were kneaded and mixed with 2 parts by weight of the catalyst component and 1 part by weight of the reactor component on a mixing pad for 45 seconds with the use of a spatula.

EXAMPLE 6

Addition Type Silicone Impression Material

| (i) | | |
|---|---|---|
| | Vinyl polymethylsiloxane (250Ps, 25° C.) | 50 weight % |
| | Hydrogen polymethylsiloxane (320Ps, 25° C.) | 30 weight % |
| | Finely divided quartz | 20 weight % |

-continued

| | |
|---|---|
| | 100 weight % |

The ingredients (i) were charged with 6.5 weight % of peptone and 2.0 weight % of casein in a kneader, where they were sufficiently mixed and kneaded together for 1 hour into a base component.

| (ii) | Vinyl polymethylsiloxane (250Ps, 25° C.) | 89.95 weight % |
|---|---|---|
| | Zirconium silicate | 10.0 weight % |
| | Choroplatinate | 0.05 weight % |
| | | 100 weight % |

The ingredients (ii) were charged into a kneader, and were sufficiently mixed and kneaded together for 1 hour into a catalyst component.

Equal amounts of the base and catalyst components were kneaded and mixed together on a mixing pad for 30 minutes with the use of a spatula.

EXAMPLE 7

Addition Type Silicone Impression Material

Together with the ingredients (ii) of Example 6 to which 3.5 weight % of finely divided gelatin and 2.7 weight % of the nonionic surface active agent expressed in terms of the general formula: $Rf(CH_2)_lO(C_nH_{2n}O)_m$ (manufactured by Asahi Garasu K.K., and available under the trade name of Surfaron S-145) were charged in a kneader, where they were sufficiently mixed and kneaded together for 1 hour into a catalyst component.

Equal amounts of the base component prepared in Example 6 and catalyst component were kneaded and mixed together on a mixing pad for 30 seconds with the use of a spatula.

EXAMPLE 8

Addition Type Silicone Impression Material

Together with 1.5 weight % of gelatin tannate and 3.0 weight % of polyether-modified silicone oil (manufactured by Shinetsu Kagaku K.K., and available under the trade name of KF 351), the ingredients (i) of Example 6 were charged in a kneader, and were sufficiently mixed and kneaded together for 1 hour into a base component.

Together with 3.5 weight % of gelatin and 2.0 weight % of polyoxyethylene nonyl phenyl ether, the ingredients (ii) of Example 6 were charged in a kneader, and were sufficiently mixed and kneaded together for 1 hour into a catalyst component.

Equal amounts of the base and catalyst components were kneaded and mixed on a mixing pad for 30 seconds with the use of a spatula.

EXAMPLE 9

Addition Type Silicone Impression Material

Together with 6.5 weight % of peptone and 0.2 weight % of polyoxyethylene sorbitan.monoisostearic acid ester, the ingredients (i) of Example 6 were charged in a kneader, and were sufficiently mixed and kneaded together for 1 hour into a base component.

As the catalyst component, use was made of the catalyst component prepared in Example 6, which was kneaded and mixed with the base component in equal amounts on a mixing pad for 30 seconds with the use of a spatula.

EXAMPLE 10

Addition Type Silicone Impression Material

Together with 2.5 weight % of albumin tannate and 8.2 weigth % of polyether-modified silicone oil (manufactured by Shinetsu Kagaku K.K., and available under the trade name of KF 352), the ingredients (i) of Example 6 were charged in a kneader, and were sufficiently mixed and kneaded together for 1 hour into a base component.

Together with 2.0 weight % of casein and 1.0 weight % of polyoxyethylene propylene glycol-mono-fatty acid ester, the ingredients (ii) of Example 6 were charged in a kneader, and were sufficiently mixed and kneaded together for 1 hour into a catalyst component.

Equal amounts of the base and catalyst components were kneaded and mixing on a mixing pad for 30 seconds with the use of a spatula.

EXAMPLE 11

Addition Type Silicone Impression Material

Together with 10.5 weight % of albumin, the ingredients (i) of Example 6 were charged in a kneader, and were sufficiently mixed and kneaded together for 1 hour into a base component.

Together with 7.0 weight % of casein and 0.4 weight of pentaerythritol.fatty acid ester, the ingredients (ii) of Example 6 were charged in a kneader, and were sufficiently mixed and kneaded together for 1 hour into a catalyst component.

Equal amounts of the base and catalyst components were kneaded and mixed on a mixing pad for 30 seconds with the use of a spatula.

COMPARATIVE EXAMPLE 1

Condensation Type Silicone Impression Material

The ingredients (i) of Example 1 were charged in a kneader, and were sufficiently mixed and kneaded together for 1 hour into a base component.

Equal amounts of the base component and the catalyst component prepared in Example 1 were kneaded and mixed together on a mixing pad for 30 seconds with the use of a spatula.

COMPARATIVE EXAMPLE 2

Addition Type Silicone Impression Material

The ingredients (i) of Example 6 were charged in a kneader, and were sufficiently mixed and kneaded together for 1 hour into a base component.

Equal amounts of the base component and the catalyst component prepared in Example 6 were kneaded and mixed together on a mixing pad for 30 seconds with the use of a spatula.

COMPARISON EXAMPLE 3

Addition Type Silicone Impression Material

Together with 15.0 weight % of polyoxyethylene sorbitan.monostearic acid ester, the ingredients (i) of Example 6 were charged in a kneader, and were sufficiently mixed and kneaded together for 1 hour into a base component.

Equal amounts of the base component and the catalyst component prepared in Example 6 were kneaded and mixed together on a mixing pad for 30 seconds with the use of a spatula.

With the products of Examples 1 to 11 and Comparative Examples 1 to 3, testings were undertaken for setting time, wettability of the impression materials with respect to saliva, clearness of the details of impressions, wettability of the registered surface of the impressions taken with respect to gypsum slurry and surface roughness of gypsum models. The testing results are summarized in Tables 1 and 2.

fine lines, each of 25 mm in length and 10 μm, 20 μm, 50 μm or 75 μm in width, was immersed in artificial saliva for wetting according to ISO 1563. Thereafter, a sample impression material was filled and pressed in that model, immersed in water of 35° C. for 4 minutes, and was removed to take the impressions of the fine lines. The surface of the thus obtained impressions was observed under a 6 to 10-x magnifying glass, while it was illuminated at a low angle. The clearness was indicated by the width of the finest one of the lines reproduced

TABLE 1

| | | Condensation Type Silicone Impression Material | | | |
|---|---|---|---|---|---|
| | Setting Time | Wettability of impression material with respect to Saliva (angle of contact of advance of artificial saliva) | Clearness of impression details (width of fine lines reproduced) | Wettability of impression surface with respect to gypsum slurry | Surface roughness of gypsum model |
| Example 1 | 4 min 30 sec | 45° | 20 μm | Satisfactory | 2.8 μm |
| Example 2 | 4 min 30 sec | 42° | 10 μm | Very Satisfactory | 3.3 μm |
| Example 3 | 4 min 30 sec | 40° | 10 μm | Very Satisfactory | 3.6 μm |
| Example 4 | 4 min 30 sec | 47° | 20 μm | Very Satisfactory | 3.0 μm |
| Example 5 | 5 min 00 sec | 40° | 10 μm | Very Satisfactory | 3.2 μm |
| Comparison Example 1 | 4 min 30 sec | 80° | 50 μm | Unsatisfactory | 3.6 μm |

TABLE 2

| | | Addition Type Silicone Impression Material | | | |
|---|---|---|---|---|---|
| | Setting Time | Wettability of impression material with respect to saliva (angle of contact of advance of artificial saliva) | Clearness of impression details (width of fine lines reproduced) | Wettability of impression surface with respect to gypsum slurry | Surface roughness of gypsum model |
| Example 6 | 4 min 20 sec | 58° | 20 μm | Satisfactory | 2.4 μm |
| Example 7 | 4 min 30 sec | 40° | 10 μm | Very Satisfactory | 2.5 μm |
| Example 8 | 4 min 30 sec | 48° | 10 μm | Very Satisfactory | 2.7 μm |
| Example 9 | 4 min 30 sec | 43° | 10 μm | Very Satisfactory | 2.7 μm |
| Example 10 | 4 min 40 sec | 58° | 20 μm | Very Satisfactory | 3.5 μm |
| Example 11 | 4 min 40 sec | 42° | 20 μm | Very Satisfactory | 3.0 μm |
| Comparison Example 2 | 4 min 30 sec | 85° | 75 μm | Unsatisfactory | 2.7 μm |
| Comparison Example 3 | 8 min 30 sec | 45° | 10 μm | Unsatisfactory | 8.5 μm |

For the measurement of setting time, a sample was placed in a stainless steel ring of 8.0 mm in height, 24.0 mm in inner diameter and 1.0 mm in thickness in a constant temperature chamber maintained at a temperature of $23\pm2°$ C. and a humidity of $50\pm10\%$. An 150 g loaded Vicat needle (of 3.0 mm in diameter) was stuck down into the sample. The setting time was found by measuring a time span from the time of start of mixing to the time at which the needle was stuck down into the sample by only 1.0 mm or lower.

For measuring the wettability of the impression materials with respect to saliva (expressed in terms of the angle of contact of advance of artificial saliva), the artificial saliva of Green Wood was added dropwise onto the plane of a cured sample impression, which was then inclined at an angle of 6° to measure the angle of contact of advance of the artificial saliva.

For measuring the clearness of the details of a sample impression (expressed in terms of the width of fine lines reproduced), a model under test having four types of continuously over the full length.

For measuring the wettability of the impression surface with respect to gypsum slurry, dental super-hard gypsum (manufactured by GC Dental Industrial Co., and available under the trade name of Fujirock) was mixed with water in a P:W ratio of 100:20 (by weight), and the resulting mixture was cast onto the impression obtained in the clearness testing to visually observe and estimate the wettability of the gypsum slurry with respect to the impression.

For the surface roughness of a sample gypsum model, the impression of the smooth surface of a glass plate was first taken. The dental super-hard gypsum was mixed with water in a P:W ratio of 100:20 (by weight), and the resulting mixture was cast onto that impression. The gypsum was set after the lapse of 30 minutes or longer. Thereafter, the set gypsum was released from the impression, and was measured on the surface with a surface roughness meter (manufactured by Tokyo Seimitsu K.K., and available under the trade name of Surfcomb 30B) according to JIS-B0601 to obtain ten measurements which were then averaged.

As can be understood from the results of the condensation (Table 1) and addition (Table 2) type silicone impression materials, the present silicone impression materials to which the proteins soluble or slightly soluble in water were added (Examples 1 and 6) and the present silicone impression materials to which added were the combinations of the proteins soluble or slightly soluble in water with the hydrophilic nature-affording agents such as hydrophilic silicone oils and nonionic surfactants (Examples 2-5 and 7-11) show more satisfactory wettability with respect to saliva at the time of taking the impression of the oral cavity, as compared with the conventional silicone impression materials (Comparative Examples 1 and 2). Thus, since the present materials have no repelling action on saliva, they make it possible to take clear impressions of the details of the oral cavity, even when it is wetted with saliva. In addition, since the registered surface of the impression taken at the time of preparing a gypsum model shows satisfactory wettability with respect to gypsum slurry, and has no repelling action thereupon, it is possible to allow the gypsum slurry to be cast into the details of the impression surface without any entrainment of air bubbles and, hence, obtain a precise gypsum model. Further, since the amount of the hydrophilic nature-affording agents such as hydrophilic silicone oils and nonionic surfactants to be used is reduced and limited, the setting reaction of silicone rubber such as condensation or addition vulcanization is not inhibited at all. Nor is the setting reaction of gypsum inhibited. Thus, there is neither delay in the setting time nor surface roughening of gypsum models, unlike the silicone impression material (Comparative Example 3) containing a larger amount of the nonionic surface active agent.

What is claimed is:

1. A dental precise impression material comprising condensation or addition type room temperature-vulcanizing silicone, which further contains 0.1 to 10.0 weight % of at least one protein soluble or slightly soluble in water.

2. A dental precise impression material comprising condensation or addition type room temperature-vulcanizing silicone, which further contains 0.1 to 10.0 weight % of at least one protein soluble or slightly soluble in water, and 0.05 to 5.0 weight % of at least one hydrophilic nature-affording agent selected from the hydrophilic silicone oils and nonionic surface active agents.

3. The dental precise impression material of claim 1, wherein said protein is one member selected from the group consisting of albumin, globulin, gluten, histone, and protamine.

4. The dental precise impression material of claim 1, wherein said protein is one member selected from the group consisting of casein, vitellin, keratin, phosvitin, albumin tannate, and gelatin tannate.

5. The dental precise impression material of claim 1, wherein said protein is one member selected from the group consisting of gelatin, proteose, and peptone.

6. The dental precise impression material of claim 2, wherein said hydrophilic nature-affording agent is a hydrophilic silicone oil selected from the group consisting of polyether-modified silicone oil and alcohol-modified silicone oil.

7. The dental precise impression material of claim 2, wherein said nonionic surface active agent is a polyether.

8. The dental precise impression material of claim 7, wherein said polyether is one member selected from the group consisting of polyoxyethylene alkyl ether, polyoxyethylene polyoxypropylene alkyl ether, and polyoxyethylene alkyl phenyl ether.

9. The dental precise impression material of claim 2, wherein said nonionic surface active agent is a partial ester of a polyhydric alcohol with a fatty acid.

10. The dental precise impression material of claim 9, wherein said polyhydric alcohol is one member selected from the group consisting of sorbitan, glycerin, polyglycerin, ethylene glycol, polyethylene glycol, propylene glycol and pentaerythritol.

11. The dental precise impression material of claim 2, wherein said nonionic surface active agent is a mixed polyether ester of a polyhydric alcohol.

12. The dental precise impresson material of claim 11, wherein said mixed polyether ester is selected from the group consisting of polyoxyethylene sorbitan fatty acid esters, polyoxyethylene sorbitol fatty acid esters, polyoxyethylene mannitan fatty acid esters, polyoxyethylene glyceryl fatty acid esters, and polyoxyethylene propylene glycol mono-fatty acid esters.

13. The dental precise impression material of claim 2, wherein said nonionic surface active agent is an ester of the addition product of ethyleneoxide with one member of the group consisting of caster oil, lanolin, phytosterol, and beeswax.

14. The dental precise impression material of claim 2, wherein said nonionic surface active agent is one member selected from the group consisting of $Rf$—$O(C_nH_{2n}O)_nH$, $Rf(CH_2)_lO(C_nH_{2n}O)_m$, and $RfBn(R')(C_2H_4O)_nH$, wherein $Rf$ is a fluorinated aliphatic or aromatic group having 1–20 carbon atoms, B is a divalant connecting group, $R'$ is a hydrogen atom or an alkyl group having 1–20 carbon atoms, and l, m, and n each are an integer of 1–50.

* * * * *